United States Patent [19]

Bordoni et al.

[11] Patent Number: 4,823,784
[45] Date of Patent: Apr. 25, 1989

[54] AEROSOL INHALATION APPARATUS

[75] Inventors: Maurice E. Bordoni, Westtown; Ephraim Lieberman, Suffern, both of N.Y.

[73] Assignee: Cadema Medical Products, Inc., Middletown, N.Y.

[21] Appl. No.: 115,903

[22] Filed: Nov. 2, 1987

Related U.S. Application Data

[60] Continuation-in-part of Ser. No. 928,826, Nov. 10, 1986, Pat. No. 4,703,753, which is a division of Ser. No. 779,426, Sep. 24, 1985, abandoned, which is a continuation-in-part of Ser. No. 707,387, Mar. 1, 1985, Pat. No. 4,398,704, which is a division of Ser. No. 642,718, Aug. 22, 1984, Pat. No. 4,510,929, which is a continuation of Ser. No. 360,370, Apr. 30, 1982, abandoned.

[51] Int. Cl.$^4$ ................................................. A62B 7/00
[52] U.S. Cl. ........................... 128/200.14; 128/200.16; 128/200.21
[58] Field of Search ....................... 128/200.18, 200.14, 128/200.16, 200.21, 654

[56] References Cited

U.S. PATENT DOCUMENTS

| | | | |
|---|---|---|---|
| 3,695,254 | 10/1970 | Blum | 128/7.1 X |
| 3,915,386 | 10/1975 | Vora | 128/200.18 X |
| 4,251,033 | 2/1981 | Rich et al. | 128/200.21 X |
| 4,333,450 | 6/1982 | Lester | 128/200.14 |
| 4,402,315 | 9/1983 | Tsuda et al. | 128/200.18 |

Primary Examiner—Edward M. Coven
Attorney, Agent, or Firm—Leonard Bloom

[57] ABSTRACT

An aerosol inhalation apparatus includes a disposable aerosol inhalation device for use in producing properly sized particles as a mist. The disposable device includes a nebulizer, a first conduit, a second conduit, a third conduit and a fourth conduit. Exhalation to an entrapping filter is effected via the third conduit which has a one-way valve therein. The first and second conduits respectively communicate with a baffled nebulizer and the ambient, a one-way valve being provided within the second conduit. A further one-way valve may be provided in the first conduit to prevent a subject from exhaling therethrough, while allowing the aerosol to pass out of the nebulizer. A further one-way valve may be provided in the fourth conduit to allow fluid communication from the second conduit and the first conduit into fourth conduit in one embodiment, while preventing fluid communication from the fourth conduit to the first and second conduits an to the nebulizer. The optimum range of particle sizes is generated by producing an aerosol in the nebulizer which has an internal baffle, the sizes being in the range of from substantially 1.0 micron to substantially 3.0 microns. An air compressor is provided to supply compressed air to the nebulizer, which contains a solution of the medication sought to be supplied to a patient. The flow of compressed air is thruput to the patient at a rate of about ten liters per minute and can be interrupted.

25 Claims, 4 Drawing Sheets

AEROSOL INHALATION APPARATUS

CROSS REFERENCE TO RELATED APPLICATIONS

This application is a continuation-in-part of application Ser. No. 928,826 filed Nov. 10, 1986 U.S. Pat. No. 4,703,753 and entitled "RADIOACTIVE AEROSOL INHALATION APPARATUS AND METHOD" which, in turn, is a division of application Ser. No. 779,426 filed Sept. 24, 1985 abandoned and entitled "RADIOACTIVE AEROSOL INHALATION DEVICE AND METHOD". The application Ser. No. 779,426 is a continuation-in-part of Ser. No. 707,387 filed Mar. 1, 1985 U.S. Pat. No. 4,398,704 and entitled "AEROSOL INHALATION DEVICE AND METHOD". The Ser. No. 707,387 application is a division of application Ser. No. 642,718 filed on Aug. 22, 1984 U.S. Pat. No. 4,510,929 and entitled "DISPOSABLE RADIOACTIVE AEROSOL INHALATION APPARATUS" which is a file wrapper continuation of application Ser. No. 360,370 filed on Apr. 30, 1982 abandoned and entitled "DISPOSABLE AEROSOL INHALATION APPARATUS". The disclosure of the copending application Ser. No. 928,826 is incorporated herein in its entirety by reference.

BACKGROUND OF THE INVENTION

This invention relates to an aerosol inhalation apparatus which includes a disposable pulmonary inhalation device which includes means to generate properly sized aerosol particles, more particularly such particles containing aerosolized pentamidine isethionate for inhalation. The invention is significant for therapy and/or prophlaxsis of pneumonia and, in particular, *Pneumocystis carinii* pneumoniia (PCP), and the like.

The invention is especially useful for aerosolizing the solution to the proper aerosol particle size, and to collect the aerosol particles in a proper filter to avoid environmental and/or ambient contamination. The device is suitable for delivering aerosols to a subject undergoing treatment or prophlaxsis.

Relevant prior art United States Letters Patents are:

| U.S. Pat. No. | Inventor(s) | Date Issued |
|---|---|---|
| 3,097,645 | Lester | Jul. 16, 1963, |
| 3,172,406 | Bird et al. | Mar. 9, 1965, |
| 3,243,100 | Adams | Mar. 29, 1966, |
| 3,666,955 | Suprenant et al. | May 30, 1972, |
| 3,695,254 | Blum | Oct. 3, 1973, |
| 3,762,409 | Lester | Oct. 2, 1973, |
| 3,769,967 | Jones et al. | Nov. 6, 1973, |
| 3,777,742 | Aumiller et al. | Dec. 11, 1973, |
| 3,881,463 | Le Mon | May 6, 1975, |
| 3,976,050 | Glasser et al. | Aug. 24, 1978 and |
| 4,116,387 | Kremer, Jr. et al. | Sep. 26, 1978. |

SUMMARY OF THE INVENTION

The present invention relates to a new and improved aerosol inhalation apparatus which generates properly sized particles for the treatment and/or prophlaxis of pneumonia, in particular *Pneumocystis carinii* pneumonia (PCP). A solution containing the prophlactic and/or therapeutic agent is added to a baffled nebulizer and the solution aerosolized using compressed air. The aerosolized particles are then breathed into the lungs. The aerosol is administered to the patient through a mouthpiece or face mask or a tubular trachea-communicating member, via a conduit.

The principal aim of the present invention is to provide an aerosol inhalation apparatus which provides a site-specific, and hence less toxic, method of therapy and/or prophylaxis for diseases of the lung, in particular for *Pneumocystis carinii* pneumonia (PCP).

It is, therefore, a principal object of the present invention to provide an apparatus which includes a disposable aerosol inhalation device capable of delivering properly sized particles to lung areas, controlling delivery and recovery of aerosolized particles and exhalent materials to minimize ambient and/or environmental contamination.

Another object of the invention is to provide an apparatus which incorporates a conduit and valve arrangement which is activated during the breathing cycle of the patient or subject to assist in permitting the individual to inhale and exhale with the minimum of effort during the generation of aerosol from within the system.

An additional object of the invention is to provide an apparatus which incorporates a conduit and valve arrangement which allows an individual to breathe with minimum effort during generation of aerosol from within the apparatus.

A further object of the invention to provide an aerosol inhalation apparatus for supplying mist to a subject which is simple and inexpensive.

A still additional object of the invention is to provide an apparatus of the character described which will minimize the use of the medication.

A still further object of the invention is to provide an apparatus of the character described in which disease involving the alveolar sites of the lung can be effectively treated.

A yet additional object of the invention is to provide an apparatus of the character described which avoid contamination of the facilities, the equipment, and most importantly, the attending medical personnel to the medication being delivered and to disease-causing agents.

A yet further object of the invention is to provide an apparatus which effects the delivery of medication in an aerosol mist which is economical.

The present invention can be viewed as an aerosol inhalation apparatus for supplying an aerosol mist to a subject, a disposable aerosol inhalation device being provided. The device includes a nebulizer having a compressed air inlet and an outlet for an aerosol mist generated therein. A first conduit is in fluid communication with the outlet of the nebulizer. A second conduit, having a first one-way valve therein, provides one-way fluid communication from ambient to an intersection between the first conduit and the second conduit. A third conduit provides fluid communication from the intersection between the first conduit and the second conduit, a second one-way valve being positioned in the third conduit for providing one-way fluid communication from the intersection to ambient via a filter. A fourth conduit provides fluid communication between an airway of a patient and the intersection. The apparatus further includes a source of compressed air and means for coupling the source of compressed air to the inlet of the nebulizer.

From a slightly different aspect the invention can be seen as an aerosol inhalation apparatus for supplying an aerosol mist to a subject which includes a disposable aerosol inhalation device. The device includes a nebulizer having a compressed air inlet and an outlet for an aerosol mist generated therein. A first conduit is in fluid communication with the outlet of the nebulizer. A second conduit, having a first one-way valve therein, provides one-way fluid communication from ambient to a first intersection between the first conduit and the second conduit. The device has a third conduit and a fourth conduit, the third conduit being connected to the fourth conduit at a second intersection. A second one-way valve in the third conduit provides one-way fluid communication from the second intersection to ambient via a filter. The fourth conduit provides fluid communication between the second intersection and an airway of a patient. A third one-way valve is positioned in the fourth conduit between the first intersection and the second intersection for allowing flow from the first intersection toward the second intersection while preventing flow in reverse direction. The apparatus includes a source of compressed air and means for coupling the source of compressed air to the inlet of the nebulizer.

From one subcombination aspect the invention can be viewed as a disposable aerosol inhalation device, the device including a nebulizer having a compressed air inlet and an outlet for an aerosol mist generated therein. A first conduit is in fluid communication with the outlet of the nebulizer. A second conduit, having a first one-way valve therein, provides one-way fluid communication from ambient to an intersection between the first conduit and the second conduit. A third conduit provides fluid communication from the intersection between the first conduit and the second conduit, via a second one-way valve positioned therein, to ambient, via a filter. A fourth conduit provides fluid communication between an airway of a patient and the intersection.

From a slightly different subcombination viewpoint, the invention can be viewed as a disposable aerosol inhalation device which includes a nebulizer having a compressed air inlet and an outlet for an aerosol mist generated therein. A first conduit is in fluid communication with the outlet of the nebulizer. A second conduit having a first one-way valve therein, provides one-way fluid communication from ambient to a first intersection between the first conduit and the second conduit. A third conduit and a fourth conduit are provided. The third conduit is connected to the fourth conduit at a second intersection. A second one-way valve positioned in the third conduit provides one-way fluid communication from the second intersection to ambient via a filter. The fourth conduit provides fluid communication between the second intersection and an airway of a patient, a third one-way valve being positioned in the fourth conduit between the first intersection and the second intersection for allowing flow from the first intersection toward the second intersection, while preventing flow in reverse direction.

The source of compressed air desirably comprises an air compressor.

The air compressor preferably is an air compressor which generates about 35 to 50 pounds per square inch and supplies a thruput to the patient of about 8 to 10 liters per minute via the device.

A mouthpiece may be connected to an end of the fourth conduit for conducting air and aerosol mist from the fourth conduit to the mouth of a patient and for conducting exhaled material therefrom into the fourth conduit.

A third one-way valve may be positioned between the outlet from the nebulizer and the intersection between the first and second conduits for allowing flow toward the intersection and preventing flow from the intersection toward the nebulizer.

The nebulizer is preferably a baffled nebulizer which provides mist particles in a range of from substantially one micron in diameter to substantially three microns in diameter.

The nebulizer has reservoir portion for holding a solution, the solution may be an aqueous solution of pentamidine isethionate.

Means positioned between the compressor and the nebulizer are provided for interrupting air flow from the compressor to the nebulizer. The means positioned between the compressor and the nebulizer includes an opening to ambient which, when open, interrupts air flow from the compressor to the nebulizer and, when closed, allows air to pass into the nebulizer from the compressor. The opening is of such a diameter that it may be covered by a person's finger to effect the opening and closing thereof.

DESCRIPTION OF THE PREFERRED EMBODIMENTS

Figure 1:
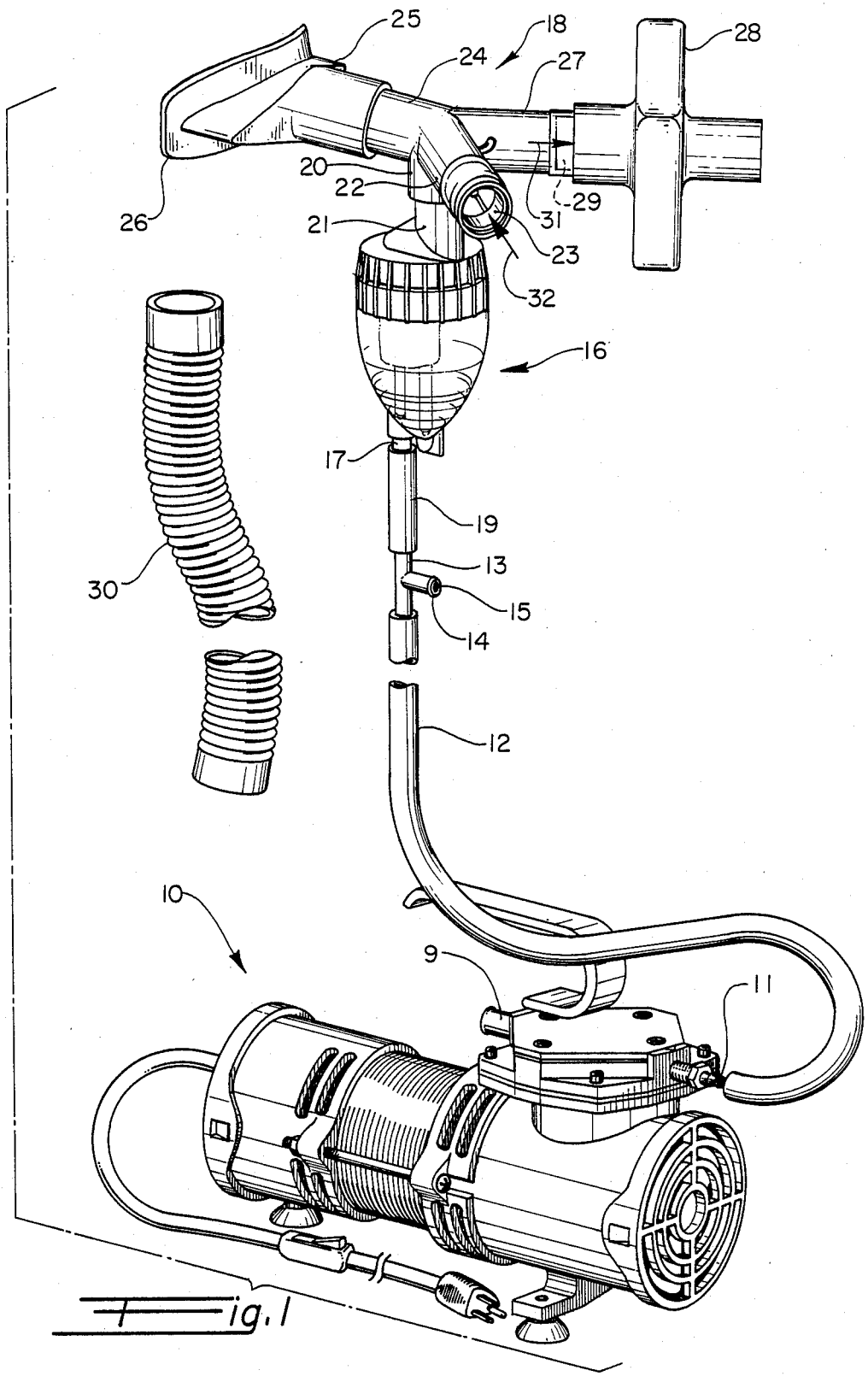
FIG. 1 is a perspective view of a first exemplary embodiment of an aerosol inhalation apparatus constructed in accordance with the present invention.

FIG. 1 illustrates a first preferred embodiment of an aerosol inhalation apparatus suitable for treating and/or prophlasis of pneumonia and other disorders of the lungs, as well as other diseases and disorders involving medications which can be dispensed in aerosol form. In particular, the apparatus is especially useful in treating patients who have *Pneumocystis carinii* pneumonia (PCP) or who are especially susceptible to this disease with pentamidine isethionate in an aqueous solution. Persons who have acquired immune deficiency syndrome (AIDS) or exhibit aids-related-complex (ARC) symptoms are believed to be helped to a considerable degree by such treatment.

The apparatus of FIG. 1 includes an electric a.c. motor driven compressor, the motor-compressor being designated generally by the numeral 10. In a realized embodiment, a motor-compressor unit available commercially under Model designation MDA-P109-AA from the Gast Mfg. Corp. of Benton Harbor, Mich. was used. The motor-compressor 10 is used to generate compressed air at a pressure of about 35–50 (and preferably 40) pounds per square inch and, in use provides a flow rate of about 8 to 10 liters per minute thruput to a patient. Ambient air is supplied to the motor-compressor 10 via an inlet illustrated by a tubular member 9. The compressed air from the motor-compressor 10 exits from a threaded fitting 11 and into a flexible conduit 12, the output end of which is positioned over an end of a T-shaped coupler 13 having an internal bore in fluid communication with an end of a further flexible conduit 19, the other arm 14 of T-shaped coupler 13 is provided with a bore 15 which provides fluid communication from the internal bore within the coupler 13 to the ambient. The purpose of the bore 15 is to provide a means for allowing the compressed air from the motor-compressor 10 to exhaust to the ambient unless a person treating a patient or the patient places a finger over the bore 15, causing the compressed air from the conduit 12 to enter the conduit 19 and be passed into a baffled nebulizer 16, via a hollow stem 17. The baffled nebulizer 16 is shown in more detail in FIG. 2 to which reference is to be made hereinbelow.

In fluid communication with the interior of the nebulizer 16 is four-way conduit assembly formed as a integral unit 18 of a plastic. The integral unit 18 includes a first conduit 20 which fits over an outlet 21 from the nebulizer 16. A second conduit 22 having a one-way flap valve 23 therein provides a one-way path for ambient air to enter the unit 18, as indicated by the arrowheaded line 32, and mix with the mist and compressed air from the nebulizer 16, an intersection being provided between the first conduit 20 and the second conduit 22. The one-way valve 23 prevents the aerosol mist and air from the motor-compressor 10 as well as exhaled materials from a patient from being passed to the ambient.

The air supplied from the ambient via the one-way valve 23 and the conduit 22 with the aerosol mist from the nebulizer 16 is inhaled by the patient via a fourth conduit 24 and a mouthpiece 25 provided with a flexible rim 26, the patient or a therapist merely placing his or her finger over the bore 15 in the coupler 13 to produce the aerosol mist from a solution containing the treating agent which has been positioned within a reservoir portion of the nebulizer 16. It is to be understood that a trigger-operated valve arrangement or the like can be used in place of the fitting 13. In either case the treating agent, which is expensive, is conserved and the breathing of the patient made easier. A third conduit 27 extends from the intersection of the conduits 20, 22 and 24 to a bacteria-viral filter 28, via a one-way valve 29 which allows the patient to exhale into the ambient as indicated by the arrowheaded line 31, the filter 28 removing microorganisms, including viruses, and the aerosolized treating agent. In a realized embodiment of the apparatus, a commercially available filter sold under the Model No. 0811 by Amici Inc. of 740 Walnut Street, Rogersford, Pa. was used. Thus, the environment and personnel are protected.

In the event one wishes to place the patient at some distance from the unit 18, the mouthpiece 25 may be removed from the end of the fourth conduit 24 and a flexible tubular conduit 30 positioned between the mouthpiece 25 and the open end of the conduit 24. The unit consisting of the nebulizer 16, the filter 28, the unit 18 and the mouthpiece 25, as well as the conduit 30, can be discarded after use and is intended for single patient use.

The details of the preferred nebulizer 16 (FIG. 1) is illustrated in FIG. 2, a cross-section having been taken axially through the nebulizer 16. The nebulizer 16 includes the stem-like, tubular conduit 17 which is positioned into the upstanding portion of the flexible conduit 19 (FIG. 1). The tubular conduit 17 is fluid communication with a vertically extending tubular member 136 which has a narrowing conical end portion terminating in an opening 137, compressed air under positive pressure from the motor-compressor 10 (FIG. 1) is to pass through the tubular member 136 and out the small opening 137. The opening 137 exhausts into a chamber 138 which is in fluid communication with a downwardly extending tubular member 140 having an opening in its lower end 141 so as to be beneath the level of liquid which may be an aqueous solution of pentamidine isethionate (300 mg. in six ml. of distilled water is a recommended dosage) which is to be placed in the bottom portion 142, which acts as a reservoir, of the interior of the nebulizer 101. The solution which is to be placed in the bottom portion of the nebulizer 16 is placed in the nebulizer by unthreading its upper portion 147 from the lower portion and placing the solution into a chamber 148 defined by the lower portion.

In close vicinity to the opening 137 and in the top portion of the chamber 138 is an aperture 144 having a relatively larger diameter portion at its uppermore end. The aperture 144 is positioned in close vicinity and immediately beneath a protrusion 145 which has a generally smooth arcuate outer surface. Positioned over the above-discussed structure and above the protrusion 145 is a baffle 146. The baffle 146 is force-fit over the structure defined by the tubular members 136 and 140, the chamber 138 and the protrusion 145. The baffle 146 has a smooth, arcuate inner surface on which droplets of liquid formed from aerosol mist particles having greater than three microns in diameter are collected, these particles running down the inner side walls of the baffle 146 so as to again collect in the bottom portion 142 of the nebulizer 101. The particle size is a function of nebulizer type, baffling and air pressure, these parameters are desirably selected to provide particles in the selected range which results in good alveolar deposition. The particles have a Gaussian distribution within the range. The range may be changed to effect a more effective deposition at diseased sites. The nebulizer 16 is constituted by the two major portions, the upper portion 147 being threadedly connected to the bottom portion, the upper portion defining internally a fluid passageway from the interior chamber 148 of the bottom portion of the nebulizer 16 and defining a passageway from the aerosol containing chamber 148. A throttle 150 is provided in the passageway between the interior chamber 148 and the tubular conduit 21, the passageway constituting a pre-determined restriction, so far as cross-section is concerned, to allow selection of the desired and/or prescribed amount of material which a patient is to inhale during a given treatment session. The throttle 150 is constituted by a plurality of downwardly extending triangularly shaped extensions **150*a*–150*c*, these extensions being bendable (when subjected to a heat treatment) so as to provide selectively a particular opening area from the chamber 148 into the rigid tubular conduit 21. As illustrated, the triangular extensions 150*a*–150*c*** are shown unbent in positions providing a maximum opening area. Were one to desire a more restrictive opening, so as to subject a subject to a lesser dose of material, the end portions of the triangular extensions 150a–150c would simply be bent inwardly so as to make the opening smaller in area. As a practical matter a number of threaded upper members 147, possibly color coded, could be provided so that a user could select which throttle opening area feature was desired in a given case.

Figure 2:
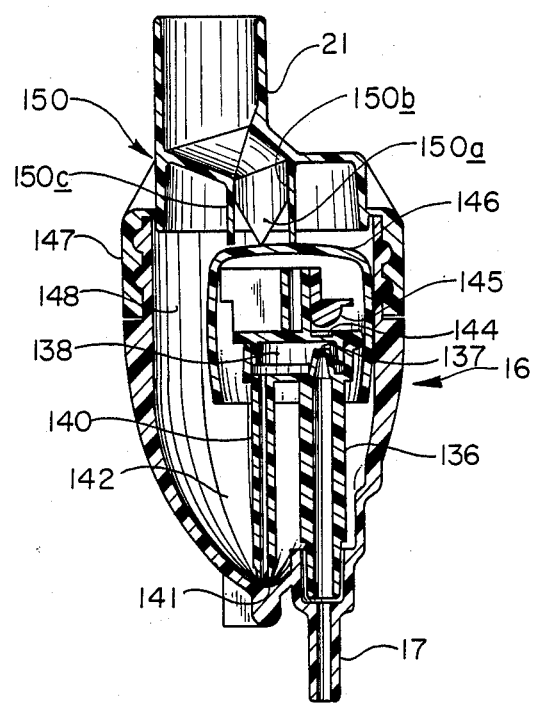
FIG. 2 is a fragmentary perspective diagrammatic view of a portion of the apparatus of FIG. 1 illustrating a nebulizer with its internal baffle which is suitable for use in the aerosol inhalation apparatus illustrated in FIG. 1.
Figure 3:
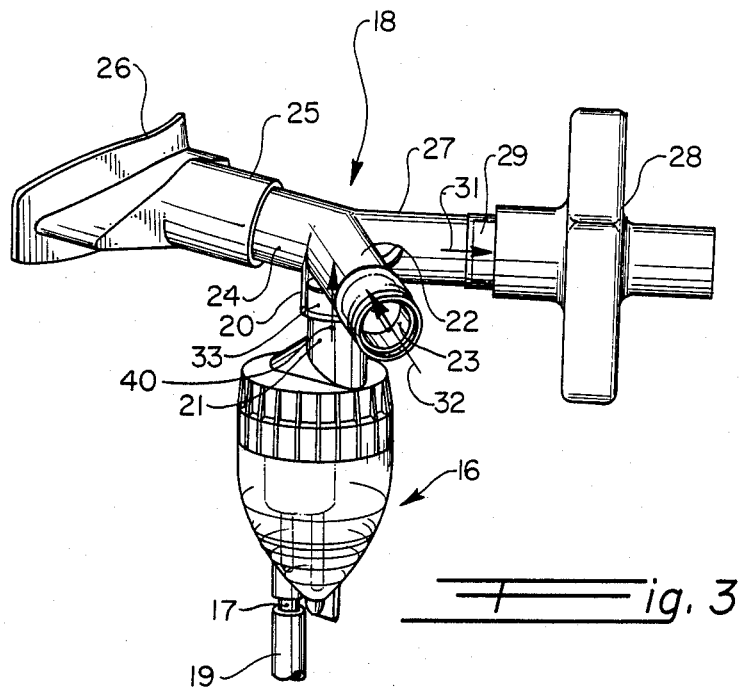
FIG. 3 is a fragmentary perspective diagrammatic view of a conduit and filter arrangement, which may be used as a substitute for a portion of the aerosol inhalation apparatus of FIG. 1, in accordance with a second exemplary embodiment of the present invention.

FIG. 3 illustrates a second preferred embodiment of an aerosol inhalation device suitable for treating and/or prophlasis of pneumonia, and the like. The device of FIG. 3, like the device of FIG. 1, includes a baffled nebulizer 16 provided with a hollow stem 17. The baffled nebulizer 16 may be constructed as shown in FIG. 2.

The device shown in FIG. 3 includes an integral unit 18 which is identical to the unit 18 (FIG. 1). The device differs in that a third one-way valve 33 is positioned within the conduit 20 for allowing aerosol mist to flow from the nebulizer 16 into the intersection provided between the first conduit 20 and the second conduit 22, as illustrated diagramatically by an arrowheaded line 40. The one-way valve 23 prevents material exhaled by a patient from entering the nebulizer 16. If desired the device 18 as shown in FIG. 3 may be used in conjunction with the flexible conduit 30 (FIG. 1).

Figure 4:
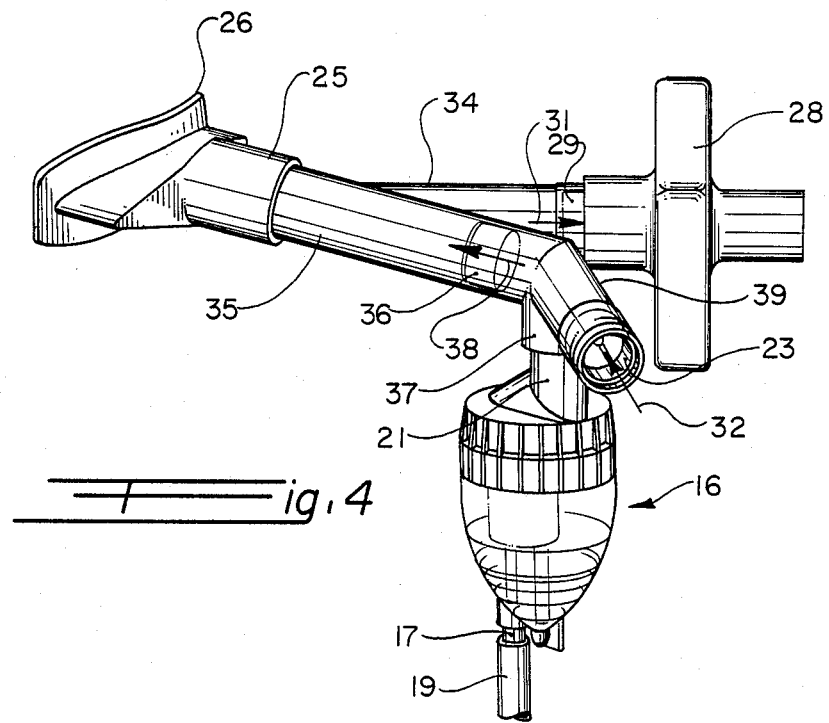
FIG. 4 is a fragmentary perspective diagrammatic view of a conduit and filter arrangement, which may be used as a substitute for a portion of the aerosol inhalation apparatus of FIG. 1, in accordance with a third exemplary embodiment of the present invention.

FIG. 4 illustrates a third preferred embodiment of an aerosol inhalation device suitable for treating and/or prophlasis of pneumonia, and the like. The device of FIG. 3, like the device forming a portion of the apparatus illustrated in FIG. 1, includes a baffled nebulizer 16 provided with a hollow stem 17, which may be placed into an open end of the flexible conduit 19 (FIG. 1). The baffled nebulizer 16 is shown in detail in FIG. 2.

In fluid communication with the interior of the nebulizer 16 is a three-way passage formed as a integral unit of a plastic. The integral unit includes a first conduit 37 which fits over an outlet 21 from the nebulizer 16. A second conduit 39 having a one-way flap valve 23 therein provides a one-way path for ambient air to enter the unit and mix with the mist and compressed air from the nebulizer 16, an intersection being provided between the first conduit 37 and the second conduit 39. The one-way valve 23 prevents the aerosol mist and air form the motor-compressor 10 (FIG. 1) from being passed to the ambient, as illustrated diagramatically by an arrowheaded line 32.

The air supplied from the ambient via the one-way valve 23 and conduit 39 with the aerosol mist from the nebulizer 16 is inhaled by the patient via a fourth conduit 35 and a mouthpiece 25 provided with a flexible rim 26, the patient or a therapist merely placing his or her finger over the bore 15 (FIG. 1) in the coupler 13 (FIG. 1) to produce the aerosol mist from a solution containing the treating agent which has been positioned within the nebulizer 16. A third one-way valve 36 is provided within the fourth conduit 35 to allow air and aerosolized mist to flow towards the mouthpiece 25, as illustrated by the arrowheaded line 38, while preventing reverse flow. A third conduit 34 extends from an intersection with the fourth conduit 35 to a bacteria-viral filter 28, via a one-way valve 29 which allows the patient to exhale into the ambient, the filter 28 removing microorganisms, including viruses, and the aerosolized treating agent. In a realized embodiment of the apparatus, a commercially available filter sold under the Model No. 0811 by Amici Inc. of 740 Walnut Street, Rogersford, Pa. was used. Thus, the environment and personnel are protected. The device shown in FIG. 4 can be discarded after use and is intended for single patient use.

Figure 5:
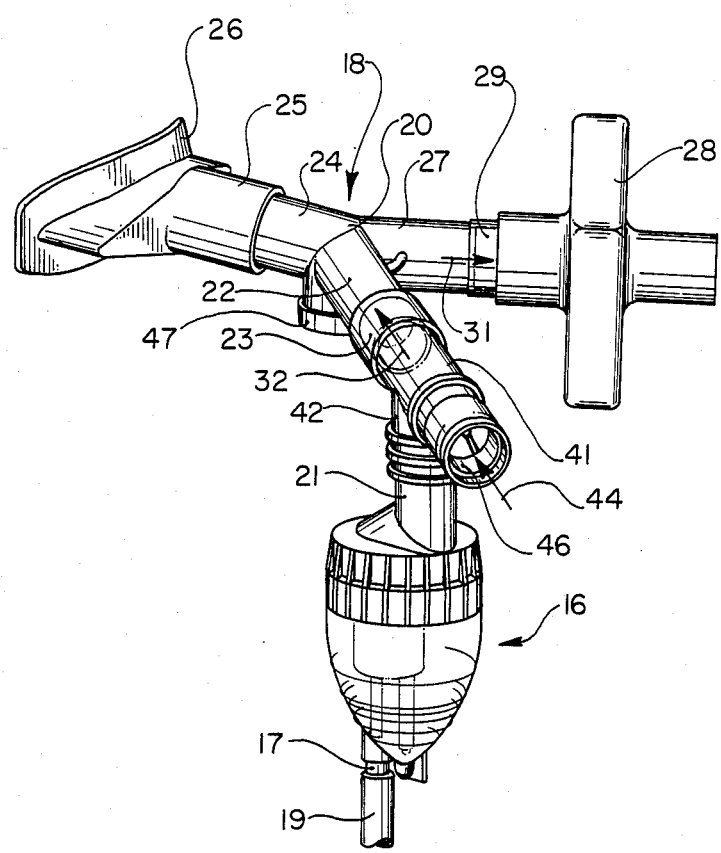
FIG. 5 is a fragmentary perspective diagrammatic view of a conduit and filter arrangement, which may be used as a substitute for a portion of the aerosol inhalation apparatus of FIG. 1, in accordance with a fourth exemplary embodiment of the present invention.

FIG. 5 illustrates a third preferred embodiment of an aerosol inhalation device suitable for treating and/or prophlasis of pneumonia, and the like. The device of FIG. 5, like the device forming a portion of the apparatus of FIG. 1, includes a baffled nebulizer 16 which includes a hollow stem 176 which is to be placed into the open end of the flexible conduit 19 (FIG. 1).

In fluid communication with the interior of the nebulizer 16, as shown in FIG. 5, is a conduit 42 which extends downwardly from an intersection with a tubular extension 41 fitted into the open end of the second conduit 22 of the unit 18 which is constructed identically to the disposable unit 18. A third one-way valve 46 is positioned within the tubular extension 41 to permit intake of air from ambient, as indicated diagramatically by the arrowheaded line 44, while preventing outflow of exhalent material, compressed air and mist. The integral unit 18 includes a first conduit 20 which may fit over the outlet 21 from the nebulizer 16, were the nebulizer 16 removed from its illustrated position, and a cap 47 removed from the open end of the conduit 20. Were this done and the extension 41 removed, the resulting structure would be identical to the device of FIG. 1. The second conduit 22, having a one-way flap valve 23 therein, provides a one-way path for ambient air, the mist and compressed air from the nebulizer 16, an intersection being provided between the first conduit 20 and the second conduit 22. The one-way valve 44 prevents the aerosol mist and air from the motor-compressor 10 from being passed to the ambient when configured as shown in FIG. 5 and the one-way valve 23 permits passage of the aerosol mist, compressed air and ambient to the patient via the second conduit 22 and the fourth conduit 24, as indicated by the arrowheaded line 32.

The air supplied from the ambient via the one-way valves 23 and 46, via the conduit 22 with the aerosol mist from the nebulizer 16 is inhaled by the patient via the fourth conduit 24 and the mouthpiece 25 provided with the flexible rim 26, the patient or a therapist merely placing his or her finger over the bore 15 (FIG. 1) in the coupler 13 (FIG. 1) to produce the aerosol mist from a solution containing the treating agent which has been positioned within the nebulizer 16. The fourth conduit 27 extends from the intersection of the conduits 20, 22 and 24 to a bacteria-viral filter 28, via the one-way valve 29 which allows the patient to exhale into the ambient, as indicated diagramatically by the arrowheaded line 31. The filter 28 removes microorganisms, including viruses, and the aerosolized treating agent. The unit consisting of the nebulizer 16, the filter 28, the unit 18, the extension 41 with its valve 46 and the mouthpiece 25 can be discarded after use and is intended for single patient use. The embodiment illustrated in FIG. 5 allows one to, in effect, select one of two treatment configurations from one group of parts. The configurations are essentially the configurations shown in FIGS. 3 and 4.

The apparatus and device of the present invention are believed to be suitable for delivery of medications other than the one mentioned above. Among the medications which may be appropriate for aerosol delivery are trimetrexate, dapsone, fansidar, bactrium and leucovorin. Many different types of one-way valves could be used in practicing the invention. The valve disclosed in the copending application Ser. No. 928,826 of applicants has been found in realized embodiments of the invention to be both suitable and inexpensive.

From the foregoing it will be seen that applicants' pulmonary inhalation apparatus and device provides for a disposable aerosol inhalation device which generates properly sized particles having provisions for proper valving, and ease of operation. Further, the apparatus and device has been described with reference to particular embodiments which have been set out, not by way of limitation, but by way of illustration. The embodiments of the apparatus and the device can be used in conjunction with ventilators and respirators, appropriate controlled valves being added. It is to be appreciated that many other embodiments and variants are possible within the spirit and scope of the invention, its scope being defined by the appended claims.

What is claimed is:

1. An aerosol inhalation apparatus for supplying an aerosol mist to a subject comprising:
    a disposable aerosol inhalation device, the device including a nebulizer having a compressed air inlet and an outlet for an aerosol mist generated therein, a first conduit in fluid communication with said outlet of said nebulizer, a second conduit having a first one-way valve therein for providing one-way fluid communication from ambient to an intersection between said first conduit and said second conduit, a third conduit providing fluid communication from the intersection between said first conduit and said second conduit, a filter coupled to said third conduit, a second one-way valve positioned in said third conduit for providing one-way fluid communication from the intersection to ambient via said filter and fourth conduit providing fluid communication between an airway of a patient and the intersection;
    a source of compressed air; and
    means coupling said source of compressed air to said compressed air inlet of said nebulizer for delivering compressed air thereto.

2. The apparatus according to claim 1, wherein said source of compressed air comprises an air compressor.

3. The apparatus according to claim 2, wherein said air compressor comprises an air compressor which generates about 35 to 50 pounds per square inch and supplies a thruput to a patient of about 8 to 10 liters per minute via said device.

4. The apparatus according to claim 1, including a mouthpiece connected to an end of said fourth conduit for conducting air and aerosol mist from said fourth conduit to the mouth of a patient and for conducting exhalent material therefrom into the fourth conduit.

5. The apparatus according to claim 1, wherein the nebulizer is a baffled nebulizer which provides mist particles in a range of from substantially one micron in diameter to substantially three microns in diameter.

6. The apparatus according to claim 1, wherein the nebulizer has reservoir portion for holding a solution and includes a solution of pentamidine isethionate therein.

7. The apparatus according to claim 1, wherein said means coupling said source of compressed air to said compressed air inlet includes means for interrupting air flow from said source of compressed air to said compressed air inlet of said nebulizer.

8. The apparatus according to claim 7, wherein said means for interrupting air flow comprises a tubular member positioned between said source of compressed air and said compressed air inlet of said nebulizer and includes an opening in said tubular member to ambient which when open vents compressed air to ambient and when closed allows compressed air to pass into the nebulizer from the source of compressed air via said tubular member.

9. The apparatus according to claim 7, wherein the opening in said tubular member is of such a diameter that it may be covered by a person's finger.

10. An aerosol inhalation apparatus for supplying an aerosol mist to a subject comprising:
    a disposable aerosol inhalation device, the device including a nebulizer having a compressed air inlet and an outlet for an aerosol mist generated therein, a first conduit in fluid communication with said outlet of said nebulizer, a second conduit having a first one-way valve therein for providing one-way fluid communication form ambient to a first intersection between said first conduit and said second conduit, a third conduit, a fourth conduit, said third conduit being connected to said fourth conduit at a second intersection, a filter coupled to said third conduit, a second one-way valve in said third conduit for providing one-way fluid communication from said second intersection to ambient via said filter and said fourth conduit providing fluid communication between said first intersection and said second intersection, a third one-way valve positioned in said fourth conduit between said first intersection and said second intersection for allowing flow from said first intersection toward said second intersection while preventing flow in reverse direction;
    means in fluid communication with said second intersection for providing fluid communication between said second intersection and an airway of a patient;
    a source of compressed air; and
    means coupling said source of compressed air to said compressed air inlet of said nebulizer for delivering compressed air thereto.

11. The apparatus according to claim 10, wherein said source of compressed air comprises an air compressor.

12. The apparatus according to claim 10, wherein said air compressor comprises an air compressor which generates about 40 pounds per square inch and supplies a thruput to a patient of substantially ten liters per minute via said device.

13. The apparatus according to claim 10, including a mouthpiece connected to an end of said means in fluid communication with said second intersection for conducting air and aerosol mist from said fourth conduit to the mouth of a patient and for conducting exhalent material therefrom into the third conduit.

14. The apparatus according to claim 10, wherein the nebulizer is a baffled nebulizer which provides mist particles in a range of form substantially one micron in diameter to substantially three microns in diameter.

15. The apparatus according to claim 10, wherein the nebulizer has reservoir portion for holding a solution and includes a solution of pentamidine isethionate therein.

16. The apparatus according to claim 10, wherein said means coupling said source of compressed air to said compressed air inlet includes means for interrupting air flow from said source of compressed air to said compressed air inlet of said nebulizer.

17. The apparatus according to claim 16, wherein said means for interrupting air flow comprises a tubular member positioned between said source of compressed air and said compressed air inlet of said nebulizer and includes an opening in said tubular member to ambient which when open vents compressed air to ambient and when closed allows compressed air to pass into the nebulizer from the source of compressed air via said tubular member.

18. The apparatus according to claim 17, wherein the opening in said tubular member is of such a diameter that it may be covered by a person's finger.

19. The apparatus according to claim 10, wherein said fourth conduit includes a section of conduit proper within which said second intersection is present, a removable extension extending from said second conduit within which said first one-way valve is positioned, said third one-way valve being positioned within said fourth conduit between the second intersection and the extension, wherein said second intersection includes a tubular extension having an open end, a cap positioned over the open end of the tubular extension, the nebulizer being removable from said first intersection, the cap being removable from the second intersection and the removable extension with the first the second intersection and the removable from the first intersection and wherein the outlet of the nebulizer is positionable over the open end of the second intersection, whereby the apparatus may function in alternative configurations.

20. A disposable aerosol inhalation device, the device comprising a nebulizer having a compressed air inlet for receiving compressed air from a source of compressed air and an outlet for an aerosol mist generated therein, a first conduit in fluid communication with said outlet of said nebulizer, a second conduit having a first one-way valve therein for providing one-way fluid communication from ambient to an intersection between said first conduit and said second conduit, a third conduit providing fluid communication from the intersection between said first conduit and said second conduit, a filter coupled to said third conduit, a second one-way valve positioned in said third conduit for providing one-way fluid communication from the intersection to ambient via said filter and a fourth conduit providing fluid communication between an airway of a patient and the intersection.

21. A disposable aerosol inhalation device, the device comprising a nebulizer having a compressed air inlet for receiving compressed air from a source of compressed air and an outlet for an aerosol mist generated therein, a first conduit in fluid communication with said outlet of said nebulizer, a second conduit having a first one-way valve therein for providing one-way fluid communication from ambient to a first intersection between said first conduit and said second conduit, a third conduit, a fourth conduit, said third conduit being connected to said fourth conduit at a second intersection, a filter, coupled to said third conduit a second one-way valve in said third conduit for providing one-way fluid communication from said second intersection to ambient via said filter and said fourth conduit providing fluid communication between said first intersection and said second intersection, a third one-way valve positioned in said fourth conduit between said first intersection and said second intersection for allowing flow from said first intersection toward said second intersection while preventing flow in reverse direction, and means in fluid communication with said second intersection providing fluid communication between said second intersection and an airway of a patient.

22. An aerosol inhalation apparatus for supplying an aerosol mist to a subject comprising a nebulizer having a compressed air inlet for receiving compressed air and an outlet for an aerosol mist generated therein, a first conduit in fluid communication with said outlet of said nebulizer, a second conduit having a first one-way valve therein for providing one-way fluid communication from ambient to an intersection between said first conduit and said second conduit, a third conduit providing fluid communication from the intersection between said first conduit and said second conduit, a filter coupled to said third conduit, a second one-way valve positioned in said third conduit, a second one-way valve positioned in said third conduit for providing one-way fluid communication from the intersection to ambient via said filter and a fourth conduit providing fluid communication between an airway of a patient and the intersection, a source of compressed air, and means for coupling said source of compressed air to said compressed air inlet of said nebulizer for delivering compressed air thereto.

23. An aerosol inhalation apparatus for supplying an aerosol mist to a subject comprising a nebulizer having a compressed air inlet for receiving compressed air and an outlet for as aerosol mist generated therein, a first conduit in fluid communication with said outlet of said nebulizer, a second conduit having a first one-way value therein for providing one-way fluid communication from ambient to a first intersection between said first conduit and said second conduit, a third conduit, a fourth conduit, said third conduit being connected to said fourth conduit at a second intersection, a filter coupled to said third conduit, a second one-way value in said third conduit for providing one-way fluid communication from said second interaction to ambient via said filter, said fourth conduit providing fluid communication between said first intersection and said second intersection, a third one-way valve positioned in said fourth conduit between said firsts intersection and said second intersection for allowing flow from said first intersection toward said second intersection while preventing flow in reverse direction, means in fluid communication with said second intersection for providing fluid communication between said second intersection and an airway of a patient, a source of compressed air, and means for coupling said source of compressed air to said compressed air inlet of said nebulizer for delivering compressed air thereto.

24. An aerosol inhalation device comprising a nebulizer having a compressed fluid inlet for receiving compressed air form a source of compressed air and an outlet for an aerosol mist generated therein, a first conduit in fluid communication with said outlet of said nebulizer, a second conduit having a first one-way valve therein for providing one-way fluid communication from ambient to an intersection between said first conduit and said second conduit, a third conduit providing fluid communication from the intersection between said first conduit and said second conduit, a filter coupled to said third conduit, a second one-way fluid communication from the intersection to ambient via said filter and a fourth conduit providing fluid communication between an airway of a patient and the intersection.

25. An aerosol inhalation device comprising a nebulizer having a compressed air inlet for receiving compressed air form a source of compressed air and an outlet for an aerosol mist generated therein, a first conduit in fluid communication with said outlet of said nebulizer, a second conduit having a first one-way valve therein for providing one-way fluid communication from ambient to a first intersection between said first conduit and said second conduit, a third conduit, a fourth conduit, said third conduit being connected to said fourth conduit at a second intersection, a filter coupled to said third conduit, a second one-way valve in said third conduit for providing one-way fluid communication from said second intersection to ambient via said filter and said fourth conduit providing fluid communication between said first intersection and second intersection, a third one-way valve positioned in said fourth conduit between said first intersection and said second intersection for allowing flow from said first intersection toward said second intersection while preventing flow in reverse direction, and means in fluid communication with said second intersection for providing fluid communication between said second intersection and an airway of a patient.

* * * * *

UNITED STATES PATENT AND TRADEMARK OFFICE
CERTIFICATE OF CORRECTION

PATENT NO. : 4,823,784

DATED : April 25, 1989

INVENTOR(S) : Bordoni et al.

It is certified that error appears in the above-identified patent and that said Letters Patent is hereby corrected as shown below:

```
     Abstract, line 17, "an" should read -- and --.
     Column 10, line 18, "form" should read -- from --.
     Column 10, line 56, "form" should read -- from --.
     Column 11, lines 23-24, after "first", delete "the second
intersection and the" and insert therefor -- one-way valve
therein being --.
     Column 12, line 13-14, after "conduit" and before "for",
delete ", a second one-way valve positioned in said third
conduit".
     Column 12, line 24, "as" should read -- an --.
     Column 12, line 26, "value" should read -- valve --.
     Column 12, line 32, "value" should read -- valve --.
     Column 12, line 38, "firsts" should read -- first --.
     Column 12, line 50, "form" should read -- from --.
     Column 12, line 65, "form" should read -- from --.
```

Signed and Sealed this

Fifth Day of December, 1989

Attest:

JEFFREY M. SAMUELS

Attesting Officer     Acting Commissioner of Patents and Trademarks

UNITED STATES PATENT AND TRADEMARK OFFICE
CERTIFICATE OF CORRECTION

PATENT NO. : 4,823,784

DATED : April 25, 1989

INVENTOR(S) : Bordoni, et al

It is certified that error appears in the above-identified patent and that said Letters Patent is hereby corrected as shown below:

Column 7, line 30, change "Fig. 3" to --Fig. 4--.

Signed and Sealed this

Eighteenth Day of June, 1991

Attest:

HARRY F. MANBECK, JR.

*Attesting Officer*     *Commissioner of Patents and Trademarks*

REEXAMINATION CERTIFICATE (1596th)
United States Patent [19]
Bordoni et al.

[11] B1 4,823,784
[45] Certificate Issued  Nov. 26, 1991

[54] AEROSOL INHALATION APPARATUS

[75] Inventors: Maurice E. Bordoni, Westtown; Ephraim Lieberman, Suffern, both of N.Y.

[73] Assignee: Cadema Medical Products, Inc., Middletown, N.Y.

Reexamination Request:
No. 90/002,147, Sep. 25, 1990

Reexamination Certificate for:
Patent No.: 4,823,784
Issued: Apr. 25, 1989
Appl. No.: 115,903
Filed: Nov. 2, 1987

Certificate of Correction issued Dec. 5, 1989.

[51] Int. Cl.$^5$ .................... A61M 11/00; B05B 17/06; A62B 7/00
[52] U.S. Cl. .......................... 128/200.14; 128/200.16; 128/200.21
[58] Field of Search ...................... 128/200.18, 200.14, 128/200.18, 200.21, 203.12, 204.18

[56] References Cited

U.S. PATENT DOCUMENTS

| | | | |
|---|---|---|---|
| 3,172,406 | 3/1965 | Bird et al. | 128/200.18 |
| 3,243,100 | 3/1966 | Adams | 137/565 |
| 3,353,536 | 11/1967 | Bird et al. | 128/200.18 |
| 3,515,135 | 6/1970 | Flower et al. | 128/205.25 |
| 3,695,254 | 10/1972 | Blum | 128/725 |
| 3,762,409 | 10/1973 | Lester | 128/200.14 |
| 3,794,026 | 2/1974 | Jacobs | 128/202.22 |
| 3,814,091 | 6/1974 | Henkin | 128/202.22 |
| 3,836,079 | 9/1974 | Huston | 128/200.18 |
| 3,867,934 | 2/1975 | Ollivier | 128/202.22 |
| 3,990,442 | 11/1976 | Patneau | 128/203.16 |
| 4,051,847 | 10/1977 | Henkin | 128/202.22 |
| 4,660,547 | 4/1987 | Kremer, Jr. | 128/200.18 |
| 4,803,977 | 2/1989 | Kremer, Jr. | 128/200.18 |

OTHER PUBLICATIONS

Hayes, et al., *Radiology*, "Improved Radioaerosol Administration System for Routine Inhalation Lung Imaging", Apr., 1979, pp. 256–258.
Wasnich, Richard D., *Journal of Nuclear Medicine*, "A High Frequency Ultrasonic Nebulizer System for Radioaerosol Delivery", Aug. 1976, vol. 17, No. 8, p. 707.
Taplin, G. V., et al., *Lung Perfusion–Inhalation Scintigraphy in Obstructive Airway Disease and Pulmonary Embolism*, Radiologic Clinics of North America, Dec. 1978; 16 (3): 491–513.
Taplin, G. V., et al., *Atlas for Lung Imaging Using Radioaerosols*, Dec. 1979; 2-E2.
Kovacs, et al., *Seminars in the Treatment of PCP*, Apr. 1987.
Pircher, et al., *Journal of Nuclear Medicine*, "Aerosol Scans with Particles in the Submicronic Range", Aug. 1965, vol. 12, No. 6, pp. 385–386.
Mullins et al., *Journal of Nuclear Medicine*, "Improved Technique for Aerosol Inhalation Scanning", Nov. 1972, vol. 12, No. 6, pp. 872.
Montgomery, et al., Aerosolized Pentamidine as Sole Therapy for Pneumocystis Carini Pneumonia in Patients with Acquired Immunodeficiency Syndrome, The Lancet, Aug. 29, 1987; 2 (8557): 480–483.
Montgomery, A. B., Aerosolization of Pentamidine for Pneumocystis Carinii Pneumonia Sep. 1987: 1–6.
Debs, R. J., et al., Selective Enhancement of Pentamidine Uptake in the Lung by Aerosolization and Delivery in Liposomes, American Review of Respiratory Diseases Mar., 1987; 135:731–737.
Swift, D. L., Size Distribution of DTPA Aerosols Produced in the Taplin-Elam Aerosols Inhalation Apparatus, Feb. 1980: 1–12.

Primary Examiner—Edgar S. Burr

[57] ABSTRACT

An aerosol inhalation apparatus includes a disposable aerosol inhalation device for use in producing properly sized particles as a mist. The disposable device includes a nebulizer, a first conduit, a second conduit, a third conduit and a fourth conduit. Exhalation to an entrapping filter is effected via the third conduit which has a one-way valve therein. The first and second conduits respectively communicate with a baffled nebulizer and the ambient, a one-way valve being provided within the second conduit. A further one-way valve may be provided in the first conduit to prevent a subject from exhaling therethrough, while allowing the aerosol to pass out of the nebulizer. A further one-way valve may be provided in the fourth conduit to allow fluid communication from the second conduit and the first conduit into fourth conduit in one embodiment, while preventing fluid communication from the fourth conduit to the first and second conduits an to the nebulizer. The optimum range of particle sizes is generated by producing an aerosol in the nebulizer which has an internal baffle, the sizes being in the range of from substantially 1.0 micron to substantially 3.0 microns. An air compressor is provided to supply compressed air to the nebulizer, which contains a solution of the medication sought to be supplied to a patient. The flow of compressed air is thruput to the patient at a rate of about ten liters per minute and can be interrupted.

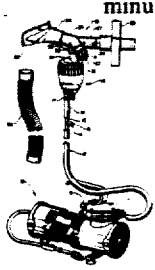

B1 4,823,784

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10-19 and 25 is confirmed.

Claims 1, 5, 6, 9 and 20-24 are determined to be patentable as amended.

Claims 2-4, 7 and 8, dependent on an amended claim, are determined to be patentable.

1. An aerosol inhalation apparatus for supplying an aerosol mist to a subject comprising:
   a disposable aerosol inhalation device, the device including a nebulizer having a compressed air inlet and an outlet for an aerosol mist generated therein, a first conduit in fluid communication with said outlet of said nebulizer, a second conduit having a first one-way valve therein for providing one-way fluid communication from ambient to an intersection between said first conduit and said second conduit, a third conduit providing fluid communication from the intersection between said first conduit and said second conduit, a filter coupled to said third conduit, a second one-way valve positioned in said third conduit for providing one-way fluid communication from the intersection to ambient via said filter and fourth conduit providing fluid communication between an airway of a patient and the intersection;
   a source of compressed air; and
   means coupling said source of compressed air to said compressed air inlet of said nebulizer for delivering compressed air thereto;
   *whereby said one-way fluid communication from ambient to the intersection between said first conudit and said second conduit eases said patient's breathing by allowing inhalation independent of said source of compressed air.*

5. The apparatus according to claim 1, wherein [the] *said* nebulizer [is a baffled nebulizer] *comprises* a hooded baffle which provides mist particles in a range of [from] substantially one micron in diameter to substantially three microns in diameter, *said range being especially suited for site-specific delivery of said particles to the lungs of said patient for treatment of pneumonia.*

6. The apparatus according to claim [1] *5*, wherein the nebulizer has *a* reservoir portion for holding a solution and includes a solution of pentamidine isethionate therein, *said range being especially suited for site-specific delivery of particles of pentamidine isethionate to the lungs of said patient for treatment of pneumocystis carinii pneumonia.*

9. The apparatus according to claim [7] *8*, wherein the opening in said tubular member is of such a diameter that it may be covered by a person's finger.

20. A disposable aerosol inhalation device, [the device] comprising a nebulizer having a compressed air inlet for receiving compressed air from a source of compressed air, *a reservoir portion for holding a solution and a solution of pentamidine isethionate therein, a hooded baffle which provides mist particles in a range of substantially one micron in diameter to substantially three microns in diameter, said range being especially suited for site specific delivery of particles of pentamidine isethionate to the lungs of said patient for treatment of pneumocystis carinii pneumonia,* and an outlet for an aerosol mist generated therein, a first conduit in fluid communication with said outlet of said nebulizer, a second conduit having a first one-way valve therein for providing one-way fluid communication from ambient an intersection between said first conduit and said second conduit, a third conduit providing fluid communication from the intersection between said first conduit and said second conduit, a filter coupled to said third conduit, a second one-way valve positioned in said third conduit for providing one-way fluid communication from the intersection to ambient via said filter and a fourth conduit providing fluid communication between an airway of a patient and the intersection.

21. A disposable aerosol inhalation device, the device comprising a nebulizer having a compressed air inlet for receiving compressed air from a source of compressed air and an outlet for an aerosol mist generated therein, a first conduit in fluid communication with said outlet of said nebulizer, a second conduit having a first one-way valve therein for providing one-way fluid communication from ambient to a first intersection between said first conduit and said second conduit, a third conduit, a fourth conduit, said third conduit being connected to said fourth conduit at a second intersection, a filter [,] coupled to said third conduit, a second one-way valve in said third conduit for providing one-way fluid communication from said second intersection to ambient via said filter and said fourth conduit providing fluid communication between said first intersection and said second intersection, a third one-way valve positioned in said fourth conduit between said first intersection and said second intersection for allowing flow from said first intersection toward said second intersection while preventing flow in reverse direction, and means in fluid communication with said second intersection *for* providing fluid communication between said second intersection and an airway of patient.

22. An aerosol inhalation apparatus for supplying an aerosol mist to a subject comprising a nebulizer having a compressed air inlet for receiving compressed air, *a reservoir portion for holding a solution and a solution of pentamidine isethionate therein, a hooded baffle which provides mist particles in a range of substantially one micron in diameter to substantially three microns in diameter, said range being especially suited for site specific delivery of particles of pentamidine isethionate to the lungs of said patient for treatment of pneumocystis carinii pneumonia,* and an outlet for an aerosol mist generated therein, a first conduit in fluid communication with said outlet of said nebulizer, a second conduit having a first one-way valve therein for providing one-way fluid communication from ambient to an intersection between said first conduit and said second conduit, a third conduit providing fluid communication from the intersection between said first conduit and said second conduit, a filter coupled to said third conduit, a second one-way valve positioned in said third conduit for providing one-way fluid communication from the intersection to ambient via said filter and a fourth conduit providing fluid communication between an airway of a patient and the intersection, a source of compressed air, and means for coupling [said] *the* source of compressed air to said compressed air inlet of said nebulizer for delivering compressed air thereto.

23. An aerosol inhalation apparatus for supplying an aerosol mist to a subject comprising a nebulizer having a compressed air inlet for receiving compressed air and an outlet for an aerosol mist generated therein, a first conduit in fluid communication with said outlet of said nebulizer, a second conduit having a first one-way valve therein for providing one-way fluid communication from ambient an intersection between said first conduit and said second conduit, a third conduit, a fourth conduit, said third conduit being connected to said fourth conduit at a second intersection, a filter coupled to said third conduit, a second one-way valve in said third conduit for providing one-way fluid communication from said second [interaction] *intersection* to ambient via said filter, said fourth conduit providing fluid communication between said first intersection and said second intersection, a third one-way valve positioned in said fourth conduit between said firsts intersection and said second intersection for allowing flow from said first intersection toward said second intersection while preventing flow in reverse direction, means in fluid communication with said second intersection for providing fluid communication between said second intersection and an airway of a patient, a source of compressed air, and means for coupling [said] *the* source of compressed air to said compressed air inlet of said nebulizer for delivering compressed air thereto.

24. An aerosol inhalation device comprising a nebulizer having a compressed fluid inlet for receiving compressed air from a source of compressed air, *a reservoir portion for holding a solution and a solution of pentamidine isethionate therein, a hooded baffle which provides mist particles in a range of substantially one micron in diameter to substantially three microns in diameter, said range being especially suited for site specific delivery of particles of pentamidine isethionate to the lungs of said patient for treatment of pneumocystis carinii pneumonia,* and an outlet for an aerosol mist generated therein, a first conduit in fluid communication with said outlet of said nebulizer, a second conduit having a first one-way valve therein for providing one-way fluid communication from ambient to an intersection between saidfirst conduit and said second conduit, a third conduit providing fluid communication from the intersection between said first conduit and said second conduit, a filter coupled to said third conduit, a second one-way fluid communication from the intersection to ambient via said filter and a fourth conduit providing fluid communication between an airway of a patient and the intersection.

* * * * *